United States Patent [19]
Wolk

[11] Patent Number: 5,681,163
[45] Date of Patent: Oct. 28, 1997

[54] DISPOSABLE RESIN APPLICATOR

[76] Inventor: Roger S. Wolk, 28 Malibu Colony, Malibu, Calif. 90265

[21] Appl. No.: 546,602

[22] Filed: Oct. 23, 1995

[51] Int. Cl.$^6$ ........................................... A61C 7/00
[52] U.S. Cl. ........................ 433/3; 433/141; 433/164
[58] Field of Search ............................ 433/3, 4, 141, 433/163, 164

[56] References Cited

U.S. PATENT DOCUMENTS

| | | | |
|---|---|---|---|
| 532,720 | 1/1895 | Dennis | 433/164 |
| 532,721 | 1/1895 | Dennis | 433/164 |
| 888,071 | 5/1908 | Dodez | 433/141 |
| 3,485,993 | 12/1969 | Miller | 433/3 |
| 4,375,961 | 3/1983 | Brooks | 433/159 |
| 4,472,137 | 9/1984 | Barone | 433/3 |

*Primary Examiner*—Cary E. O'Connor
*Attorney, Agent, or Firm*—Thomas I. Rozsa; Tony D. Chen

[57] ABSTRACT

A disposable resin applicator is used for applying a small, precise mound of resin to hold an orthodontic wire to the teeth of a patient. The disposable resin applicator assists an orthodontist to bond curing resin to the teeth to retain the wire used to stabilize the teeth after or during orthodontic movement. The resin applicator has a translucent wire bonder tip which has two opposite wire slots through which the orthodontic wire can be inserted therein. An alignment guide runs the length of the wire bonder tip on either side so that it is easy to visually view where the wire slots are to place on the orthodontic wire. The curing resin is placed in a tiny cup on the wire bonder tip and then it is placed over the orthodontic wire on the tooth so that the wire fits in the two wire slots such that the wire bonder tip can be held by a dental tool. Then a curing light is shined on the resin through the translucent wire bonder tip so that the resin becomes hardened and holds the orthodontic wire to the teeth.

26 Claims, 1 Drawing Sheet

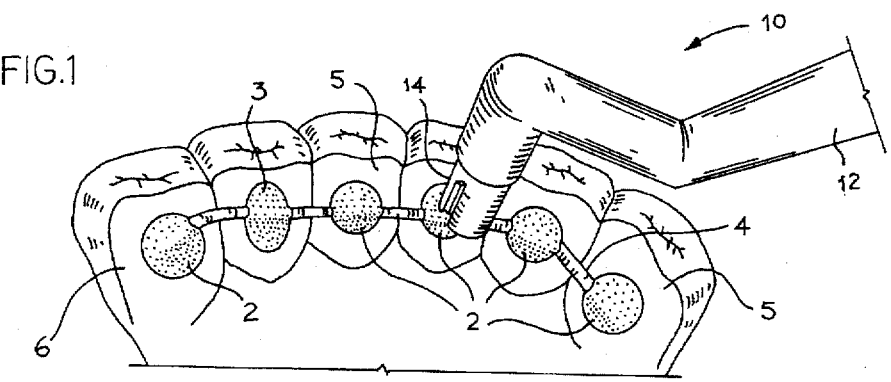
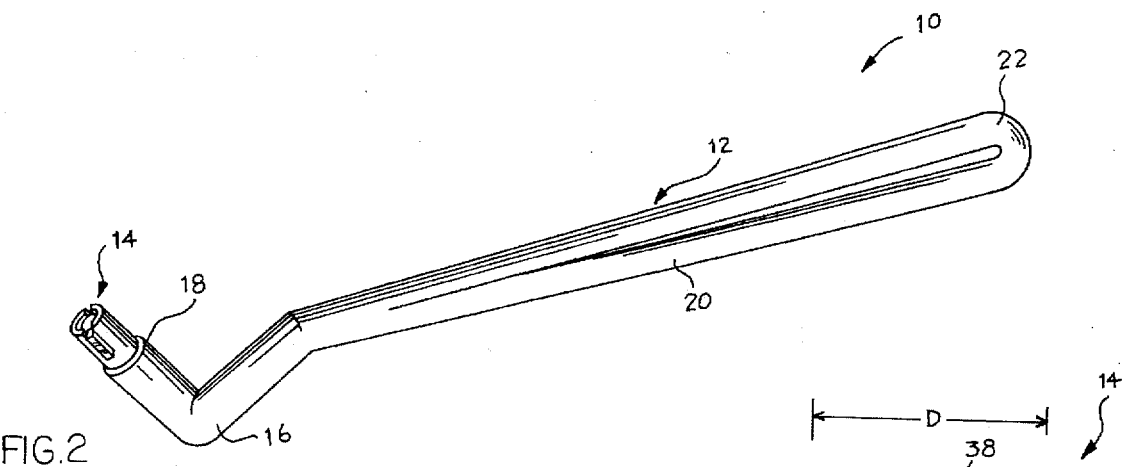
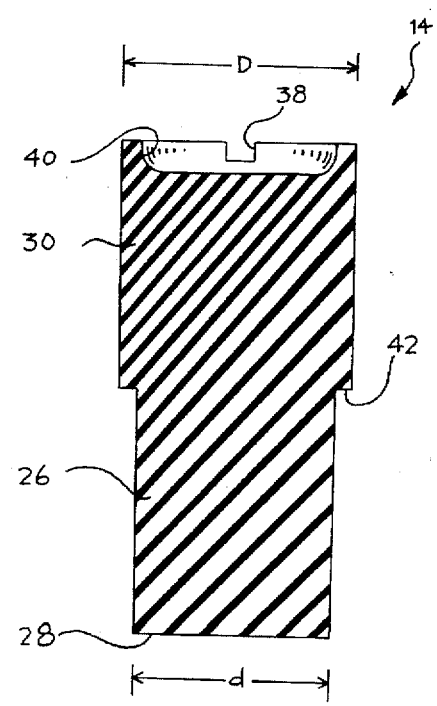

5,681,163

1

DISPOSABLE RESIN APPLICATOR

BACKGROUND OF THE INVENTION

1. Field of the Invention

The present invention generally relates to the field of dentistry. More particularly, the present invention relates to the field of orthodontics for applying a small, precise mound of curing resin to bond a lingual or labial retainer to teeth of a patient.

2. Description of the Prior Art

Presently, labial and lingual retainers are bonded to surfaces of teeth by using an applicator such as a tiny dental tool. The disadvantage in using the dental tool is that a precise amount and shape or contour for the curing resin has to be applied for bonding an orthodontic wire to the surface of each tooth. At times, the orthodontist may apply too much curing resin to bond the orthodontic wire to the surface of each tooth or does not apply enough curing resin to the orthodontic wire to keep the wire securely over each tooth. This process is time consuming and it is sloppy to apply the resin with the conventional dental tool.

Therefore, it is highly desirable to have a very efficient and also very effective design and construction of a disposable resin applicator for assisting an orthodontist to apply a small, precise mound of resin to hold the orthodontic wire to the teeth of a patient. It is also desirable to provide a disposable resin applicator with the capability of rapidly and effortless applying a neat mound of adhesive resin on each surface of the tooth for holding the orthodontic wire in place.

SUMMARY OF THE INVENTION

The present invention is a novel and unique disposable resin applicator for applying a small, precise mound of resin to hold an orthodontic wire to the teeth of a patient. The disposable resin applicator assists an orthodontist to bond curing resin to the teeth to retain the wire used to stabilize the teeth after or during orthodontic movement.

The objective is to have a translucent wire bonder tip member which has two opposite wire slots through which the orthodontic wire can be inserted therein. An alignment guide runs approximately the length of the wire bonder tip member on either side so that it is easy to visually view where the wire slots are to be placed on the orthodontic wire. The curing resin is placed in a tiny cup on the wire bonder tip member and then it is placed over the orthodontic wire on the tooth so that the wire fits in the two wire slots so that the wire bonder tip member can be held by any means such as a tool. Then curing light is shined on the resin through the translucent wire bonder tip member so that the resin becomes hardened and holds the orthodontic wire to teeth.

Alternatively, in the event self curing resin is used instead of resin that requires a curing light, then it is not necessary for the wire bonder tip to be translucent. Accordingly, it is an object of the present invention to have a non translucent wire bonder tip member which has two opposite wire slots through which the orthodontic wire can be inserted therein. An alignment guide runs approximately the length of the wire bonder tip member on either side so that it is easy to visually view where the wire slots are to be placed on the orthodontic wire. The self curing resin is placed in a tiny cup on the wire bonder tip member and then it is placed over the orthodontic wire on the tooth so that the wire fits in the two wire slots so that the wire bonder tip member can be held by any means such as a tool. The wire bonder tip is then held

2 in place until the self curing resin hardens thereby holding the orthodontic wire to the teeth.

It has been discovered, according to the present invention, that by providing a disposable resin applicator, it can be disposed of after use for preventing infectious diseases to other patients.

It has also been discovered, according to the present invention, that by providing a wire bonder tip member which has a tiny receptacle and two opposite wire slots on the periphery rim surrounding the receptacle through which an orthodontic wire can be inserted, it will consistently provide a small, precise mound of resin to hold the lingual or the labial wires to the teeth of a patient and thereby eliminate the guesswork in deciding the amount of resin to be applied.

It has additionally been discovered, according to the present invention, that by providing a wire bonder tip member with alignment guides on either side of the wire bonder tip member and aligned with the wire slots, it will provide an easy way to visually view where the wire slots are to be placed on the orthodontic wire.

It has further been discovered, according to the present invention, that by providing a translucent wire bonder tip member, it will provide an easy way for curing light to shine on the resin through the translucent wire bonder tip member so that the resin becomes hardened and holds the orthodontic wire to teeth.

It is therefore an object of the present invention to provide a disposable resin applicator so that when the resin applicator is used once, it can be disposed and thereby prevent the transmission of infectious diseases to other patients.

It is also an object of the present invention to provide a wire bonder tip member which comprises a tiny receptacle and two opposite wire slots, where an orthodontic wire can be inserted within the opposite wire slots, so that the receptacle can consistently provide a small, precise mound of resin to hold the lingual or the labial wires to the teeth of a patient without requiring guesswork as to the amount of resin to be applied.

It is an additional object of the present invention to provide a wire bonder tip member with alignment guides on either side of the wire bonder tip member and aligned with the wire slots, so that they provide an easy way to visually view where the wire slots are to be placed on the wire.

It is a further object of the present invention to provide a translucent wire bonder tip member, so that curing light can shine on the resin through the translucent wire bonder tip member and the resin becomes hardened and holds the orthodontic wire to teeth.

It is another object of the present invention to provide a wire bonder tip member that can be utilized with any common tool in the field of orthodontics such as forceps or other simple tools for holding the wire bonder tip member and applying the resin to the orthodontic wire and the teeth.

Further novel features and other objects of the present invention will become apparent from the following detailed description, discussion and the appended claims, taken in conjunction with the drawings.

BRIEF DESCRIPTION OF THE DRAWINGS

Referring particularly to the drawings for the purpose of illustration only and not limitation, there is illustrated:

FIG. 1 is an illustration, showing the present invention disposable resin applicator applying the curing resin to surfaces of teeth for bonding an orthodontic wire thereon;

FIG. 2 is a perspective view of the preferred embodiment of the present invention disposable resin applicator;

FIG. 3 is an enlarged perspective view of the wire bonder tip member of the present invention disposable resin applicator; and FIG. 4 is an enlarged cross-sectional view taken along line 4—4 of FIG. 3.

DESCRIPTION OF THE PREFERRED EMBODIMENT

Although specific embodiments of the present invention will now be described with reference to the drawings, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention as further defined in the appended claims.

Referring to FIG. 1, there is illustrated at 10 the present invention disposable resin applicator for applying curing resin 2 to surfaces 5 of teeth 6 for bonding and holding an orthodontic wire 4 in place. The general description of the present invention disposable resin applicator will be focused on lingual wires, however, it will be appreciated that the present invention disposable resin applicator 10 can be utilized for labial wires as well.

Referring to FIG. 2, there is shown at 10 a perspective view of the present invention, a disposable resin applicator, which comprises an elongated dental tool member 12 and a translucent wire bonder tip member 14. The tool member 12 has a proximal section 16 with a proximal end 18 and a distal section 20 with a distal end 22. The proximal section 16 of the tool member 12 is designed at an angle to fit within the mouth of a patient (see FIG. 1). The proximal end 18 of the tool member 12 has an opening therein for retaining the wire bonder tip member 14. The distal section 20 of the tool member 14 is shaped as a handle for grasping the tool member 14 by the orthodontist.

It will be appreciated that the dental tool member 12 is not limited to the figures as illustrated. It is emphasized that while the tool member 12 illustrated in the figures is preferred, it is also within the spirit and scope of the present invention to utilize forceps or other simple tools for retaining the wire bonder tip member 14.

Referring to FIG. 3, there is shown at 14 a perspective view the wire bonder tip member of the present invention. The wire bonder tip member 14 has a generally cylindrical shaped body 24. The cylindrical body 24 has a proximal section 26 with a proximal end 28, a distal section 30 with a distal end 32 and a circumferential sidewall 34. The distal end 32 of the body 24 has a periphery rim 36, two opposite wire slots or notches 38 located on the periphery rim 36 and a receptacle or tiny cup 40 therein surrounded by the periphery rim 36. The wire bonder tip member 14 comprises an alignment guide member or a raised rib 39 (only one is shown) which runs along the length of the body 24 on either side and located on the distal section 30. The two alignment guide members 39 are respectively aligned with the two opposite slots 38 on the periphery rim 36 of the wire bonder tip member 14 to provide the orthodontist with a visual view as to where the two opposite slots 38 are located when the distal end 32 of the cylindrical body 24 abuts against the tooth 5 as shown in FIG. 1. The wire bonder tip member 14 is a tiny translucent "cookie cutter" with built-in wire slots 38 so that the curing light can shine on the resin through the translucent body 24 such that the resin becomes hardened and holds the orthodontic wire to the surfaces of the teeth.

Alternatively, it is not necessary that the type of curing resin used be resin that requires a curing light. It is possible to also use self curing resin which simply can be held in place during the hardening process. When using self curing resin, the wire bonded tip member 14 does not have to be translucent since it is not required to have any curing light shine through it. Through use of the self curing resin, the process is the same as just described except that no curing light is required and the wire bonder tip member is simply held in place while the self curing resin hardens.

Referring to FIG. 4, there is shown at 14 a cross-sectional view of the wire bonder tip member of the present invention. From this view, the diameter "D" of the distal section 30 is greater than the diameter "d" of the proximal section 26, where an edge 42 is formed so that when the wire bonder tip member 14 is press fitted within the opening at the proximal end 18 of the tool member 12, the edge 42 rests on the rim of the of the proximal end 18 (see FIG. 2). Dimensions of the wire bonded to the teeth can vary. By way of example, the wire usually can have a diameter in the range of 14/1000 to 20/1000 of an inch. The receptacle 40 has a depth of 40/1000 of an inch (1 mm) and the depth of the two opposite slots 38 to accommodate the orthodontic wire is 30/1000 of an inch so that there is sufficient additional depth of resin material to form around and above the wire to be bonded. The diameter of the receptacle 40 is typically approximate 3½ millimeters or 140/1000 of an inch. It will be appreciated that the dimensions described above are merely one illustrative embodiment and can include many other comparable sets of dimensions.

Referring to FIGS. 1 through 3, the present invention disposable resin applicator 10 is ideal for bonding a wire retainer after the first phase or the full phase treatment, where the wire is bonded on the lingual or the labial of the incisors of the patient. If the bond comes loose, it can be removed and remade in seconds without removing the entire wire from the other teeth.

The present invention disposable resin applicator 10 is used for applying a small, precise mound of resin to each surface of the tooth to hold an orthodontic wire in place. Essentially the technique is to have the disposable resin applicator 10 that assists the orthodontist to bond curing resin to the back or front surfaces of a tooth to retain an orthodontic wire during or after orthodontic treatment. The resin doesn't have to necessarily be of the oval shape 3 but can be circular 2, oval or any other shape (see FIG. 1). The unique feature of the disposable resin applicator 10 is that it consistently forms a predetermined shape every time. The curing resin is placed in the tiny cup 40 and then it is placed over the orthodontic wire 4 behind the tooth so that the wire fits in the two opposite slots 38 so that the wire bonder tip member 14 can be held by any means such as a forceps tool. Then curing light is shined on the resin through the translucent wire bonder tip member 14 so that the resin becomes hardened and holds the orthodontic wire on the surfaces of the teeth. Also, the present invention can apply self curing resin that does not require the use of a curing light to harden the resin on the orthodontic wire and to the surfaces of the teeth.

The disposable resin applicator 10 may include means for retaining a wire to the back surfaces of teeth by providing means for retaining the curing resin during the time it is bonded with a curing light. The disposable resin applicator 10 may further have means for accommodating the orthodontic wire so that curing resin can be formed over the orthodontic wire as well as having the resin against the back surface of the teeth. The disposable resin applicator 10 may also be used to bond a wire to the surfaces of the teeth to move teeth.

The operation of the foregoing embodiment now will be described. First, the receptacle 40 is filled with the curing resin. Secondly, the receptacle 40 is placed on the tooth over the orthodontic wire, where the wire is positioned within the two opposite slots 38 and held in a desired location on the surface of the tooth while curing the resin, and thereby a bonded orthodontic wire with a small, precise mound of resin holding the orthodontic wire to the teeth of a patient is produced.

The cylindrical shaped body 24 of the wire bender tip member 14 can be made from several materials. The manufacturing process which could accommodate the construction of the wire bender tip member 14 can be injection, thermoform, etc. or other molding process. By way of example, the cylindrical shaped body 24 can be made of synthetic rubber or other suitable material. The present invention conforms to conventional forms of manufacture or any other conventional way known to one skilled in the art. In addition, the cylindrical shaped body 24 may be transparent so that curing light can shine on the resin through the wire bender tip member 14 to harden the resin or the cylindrical shaped body 24 may not be transparent, and thereby a self curing resin is utilized that does not require a curing light.

The present invention has many advantageous features including: (a) the wire bonder tip member is disposable; (b) a small, precise mound of resin is formed consistently to hold the wire to the teeth; and (c) a predetermined shape of the resin is always formed.

Defined in detail, the present invention is a disposable resin applicator for applying curing resin to bond an orthodontic wire to surfaces of teeth, comprising: (a) a cylindrical shaped body having a distal section with a distal end, a proximal section with a proximal end and a circumferential sidewall, the diameter of the distal section being greater than the diameter of the proximal section, the distal end having a periphery rim, two opposite slots located on the periphery rim and a receptacle therein, where the periphery rim surrounds the receptacle; (b) at least one alignment guide member running along the length of said cylindrical shaped body and located on said distal section and aligned with one of said two opposite slots on said periphery rim of said cylindrical shaped body to provide visual viewing of where said two opposite slots are located when said distal end of said cylindrical shaped body abuts against the orthodontic wire; (c) a tool member having a distal end and a proximal end with an opening therein; and (d) said proximal section of said cylindrical shaped body installed into said opening at said proximal end of said tool member; (e) whereby said receptacle is filled with the curing resin and placed on the orthodontic wire to bond the orthodontic wire to each surface of the teeth, where the orthodontic wire fits within said two opposite slots at said distal end of said cylindrical shaped body, thereby applying a neat mound of the curing resin on each surface of the teeth for holding the orthodontic wire in place.

Defined broadly, the present invention is an applicator, comprising: (a) a holder means for applying resin to bond a wire to surfaces of teeth and having a receptacle means for retaining the resin during the time it is bonded; and (b) means for accommodating the wire so that the resin can be formed over the wire against the teeth; (c) whereby said holder means and said receptacle means are placed on the wire to bond the wire to the teeth, where the wire is held by said means for accommodating the wire, thereby applying a neat mound of the resin on the teeth for holding the wire in place.

The present invention is defined alternatively a method for applying a neat mound of curing resin to bond a wire to teeth, the method comprising the steps of: (a) providing a wire bonder tip member having a distal end, a proximal end and a sidewall, the distal end having a periphery rim, two slots located on the periphery rim and a receptacle thereon; (b) providing a tool means; (c) installing said proximal end of said wire bonder tip member to said tool means; (d) measuring a length of the wire necessary to extend to a middle of the end teeth to be bonded; (e) preparing said teeth to be bonded; (f) filling said receptacle of said wire bonder tip member with the curing resin; (g) placing said distal end of said wire bonder tip member on the tooth with the wire fitted within the two slots; (h) pushing said receptacle of said wire bonder tip member snugly onto the tooth in position; (i) applying a curing light which is shined on the resin through said wire bonder tip member so that the resin becomes hardened and holds the wire to the tooth; (j) removing said wire bonder tip member and a neat mound of curing resin remains on the tooth to hold the wire in place; and (k) bonding the middle teeth first and proceeding distally, being sure to position the wire at each desired tooth position.

The present invention is defined broadly a method for applying a neat mound of self curing resin to bond a wire to teeth, the method comprising the steps of: (a) providing a wire bonder tip having at least two slots located and a receptacle thereon; (b) measuring a length of the wire necessary to extend to a middle of the end teeth to be bonded; (c) preparing said teeth to be bonded; (d) filling said receptacle of said wire bonder tip with the self curing resin; (e) placing said wire bonder tip on the tooth with the wire fitted within said at least two slots; (f) pushing said receptacle of said wire bonder tip snugly onto the tooth in position; (g) removing said wire bonder tip and a neat mound of resin remains on the tooth to hold the wire in place; and (h) bonding the middle teeth first and proceeding distally, being sure to position the wire at each desired tooth position.

Of course the present invention is not intended to be restricted to any particular form or arrangement, or any specific embodiment disclosed herein, or any specific use, since the same may be modified in various particulars or relations without departing from the spirit or scope of the claimed invention hereinabove shown and described of which the apparatus shown is intended only for illustration and for disclosure of an operative embodiment and not to show all of the various forms or modifications in which the present invention might be embodied or operated.

The present invention has been described in considerable detail in order to comply with the patent laws by providing full public disclosure of at least one of its forms. However, such detailed description is not intended in any way to limit the broad features or principles of the present invention, or the scope of patent monopoly to be granted.

What is claimed is:

1. A disposable resin applicator for applying curing resin to bond an orthodontic wire to surfaces of teeth, comprising:

a. a cylindrical shaped body having a distal section with a distal end, a proximal section with a proximal end and a circumferential sidewall, the diameter of the distal section being greater than the diameter of the proximal section, the distal end having a periphery rim, two opposite slots located on the periphery rim and a receptacle therein, where the periphery rim surrounds the receptacle;

b. at least one alignment guide member running along the length of said cylindrical shaped body and located on said distal section and aligned with one of said two opposite slots on said periphery rim of said cylindrical shaped body to provide visual viewing of where said two opposite slots are located when said distal end of said cylindrical shaped body abuts against the orthodontic wire;

c. a tool member having a distal end and a proximal end with an opening therein; and d. said proximal section of said cylindrical shaped body installed into said opening at said proximal end of said tool member;

e. whereby said receptacle is filled with the curing resin and placed on the orthodontic wire to bond the orthodontic wire to each surface of the teeth, where the orthodontic wire fits within said two opposite slots at said distal end of said cylindrical shaped body, thereby applying a neat mound of the curing resin on each surface of the teeth for holding the orthodontic wire in place.

2. The disposable resin applicator in accordance with claim 1 wherein said cylindrical shaped body is made of rubber material.

3. The disposable resin applicator in accordance with claim 1 wherein said cylindrical shaped body is translucent.

4. The disposable resin applicator in accordance with claim 1 wherein said tool means is forceps.

5. An applicator, comprising:

a. a holder means for applying resin to bond a wire to surfaces of teeth and having a receptacle means for retaining the resin during the time it is bonded; and b. means for accommodating the wire so that the resin can be formed over the wire against the teeth, including two opposite slots formed on said receptacle means;

c. whereby said holder means and said receptacle means are placed on the wire to bond the wire to the teeth, where the wire is held by said means for accommodating the wire, thereby applying a neat mound of the resin on the teeth for holding the wire in place.

6. The applicator in accordance with claim 5 further comprising at least one raised rib running along the length of said holder means and aligned with one of said two opposite slots to provide visual viewing of where said two opposite slots are located when said holder means abuts against the wire.

7. The applicator in accordance with claim 5 wherein said receptacle means is made of rubber material.

8. The applicator in accordance with claim 5 wherein said holder means is a dental tool.

9. The applicator in accordance with claim 8 wherein said tool is a forceps.

10. The applicator in accordance with claim 5 wherein said holder means is disposable.

11. The applicator in accordance with claim 5 wherein said holder means is translucent.

12. A method for applying a neat mound of curing resin to bond a wire to teeth, the method comprising the steps of:

a. providing a wire bonder tip member having a distal end, a proximal end and a sidewall, the distal end having a periphery rim, two slots located on the periphery rim and a receptacle thereon;

b. providing a tool means;

c. installing said proximal end of said wire bonder tip member to said tool means;

d. measuring a length of the wire necessary to extend to a middle of the end teeth to be bonded;

e. preparing said teeth to be bonded;

f. filling said receptacle of said wire bonder tip member with the curing resin;

g. placing said distal end of said wire bonder tip member on the tooth with the wire fitted within the two slots;

h. pushing said receptacle of said wire bonder tip member snugly onto the tooth in position;

i. applying a curing light which is shined on the resin through said wire bonder tip member so that the resin becomes hardened and holds the wire to the tooth;

j. removing said wire bonder tip member and a neat mound of curing resin remains on the tooth to hold the wire in place; and k. bonding the middle teeth first and proceeding distally, being sure to position the wire at each desired tooth position.

13. The method in accordance with claim 12 further comprising the step of providing two raised rib members which run along the length of said wire bonder tip member and respectively aligned with said two slots on said periphery rim of said wire bonder tip member to provide visual viewing of where said two slots are located when said distal end of said wire bonder tip member abuts against the wire.

14. A method for applying a neat mound of self curing resin to bond a wire to teeth, the method comprising the steps of:

a. providing a wire bonder tip having at least two slots located and a receptacle thereon;

b. measuring a length of the wire necessary to extend to a middle of the end teeth to be bonded;

c. preparing said teeth to be bonded;

d. filling said receptacle of said wire bonder tip with the self curing resin;

e. placing said wire bonder tip on the tooth with the wire fitted within said at least two slots;

f. pushing said receptacle of said wire bonder tip snugly onto the tooth in position;

g. removing said wire bonder tip and a neat mound of resin remains on the tooth to hold the wire in place; and h. bonding the middle teeth first and proceeding distally, being sure to position the wire at each desired tooth position.

15. The method in accordance with claim 14 further comprising the step of providing a tool means.

16. The method in accordance with claim 15 further comprising the step of installing said wire bonder tip to said tool means.

17. The method in accordance with claim 14 further comprising the step of providing at least on raised rib which runs along the length of said wire bonder tip and respectively aligned with one of said at least two slots to provide visual viewing of where said at least two slots are located when said wire bonder tip abuts against the wire.

18. A disposable resin applicator for applying curing resin to bond an orthodontic wire to surfaces of teeth, comprising:

a. a body having a distal section with a distal end and a proximal section with a proximal end, the distal end having a periphery rim, two opposite slots located on the periphery rim and a receptacle therein, where the periphery rim surrounds the receptacle;

b. at least one alignment guide member running along the length of said body and located on said distal section and aligned with one of said two opposite slots on said periphery rim of said body to provide visual viewing of where said two opposite slots are located when said distal end of said body abuts against the orthodontic wire;

c. a tool member having a distal end and a proximal end with an opening therein; and d. said proximal section of said body installed into said opening at said proximal end of said tool member;

e. whereby said receptacle is filled with the curing resin and placed on the orthodontic wire to bond the orthodontic wire to each surface of the teeth, where the orthodontic wire fits within said two opposite slots at said distal end of said body, thereby applying a neat mound of the curing resin on each surface of the teeth for holding the orthodontic wire in place.

19. The disposable resin applicator in accordance with claim 18 wherein the diameter of said distal section of said body being greater than the diameter of said proximal section of said body, thereby forming an edge so that when said proximal section of said body is installed into said opening of said tool member, the edge rests on top of said proximal end of said tool member.

20. An applicator, comprising:

a. a translucent holder means for applying resin to bond a wire to surfaces of teeth and having a receptacle means for retaining the resin during the time it is bonded; and b. means for accommodating the wire so that the resin can be formed over the wire against the teeth;

c. whereby said holder means and said receptacle means are placed on the wire to bond the wire to the teeth, where the wire is held by said means for accommodating the wire, thereby applying a neat mound of the resin on the teeth for holding the wire in place.

21. The applicator in accordance with claim 20 wherein said means for accommodating the wire so that the resin can be formed over the wire against the teeth further comprises two opposite slots formed on said receptacle means.

22. The applicator in accordance with claim 21 further comprising at least one raised rib running along the length of said holder means and aligned with one of said two opposite slots to provide visual viewing of where said two opposite slots are located when said holder means abuts against the wire.

23. The applicator in accordance with claim 20 wherein said receptacle means is made of robber material.

24. The applicator in accordance with claim 20 wherein said holder means is a dental tool.

25. The applicator in accordance with claim 24 wherein said tool is a forceps.

26. The applicator in accordance with claim 20 wherein said holder means is disposable.

* * * * *